US009901734B2

(12) United States Patent
Bennett

(10) Patent No.: US 9,901,734 B2
(45) Date of Patent: Feb. 27, 2018

(54) ELECTROSTIMULATION DEVICE WITH PERCUTANEOUS LEADS

(71) Applicant: Renee Bennett, Dearborn, MI (US)

(72) Inventor: Renee Bennett, Dearborn, MI (US)

(*) Notice: Subject to any disclaimer, the term of this patent is extended or adjusted under 35 U.S.C. 154(b) by 0 days.

(21) Appl. No.: 15/074,717

(22) Filed: Mar. 18, 2016

(65) Prior Publication Data
US 2016/0346541 A1 Dec. 1, 2016

Related U.S. Application Data

(60) Provisional application No. 62/135,079, filed on Mar. 18, 2015.

(51) Int. Cl.
A61N 1/36 (2006.01)
A61N 1/05 (2006.01)

(52) U.S. Cl.
CPC ....... A61N 1/36017 (2013.01); A61N 1/0502 (2013.01); A61N 1/36021 (2013.01)

(58) Field of Classification Search
None
See application file for complete search history.

(56) References Cited

U.S. PATENT DOCUMENTS

| 5,324,287 | A | 6/1994 | Szeles |
| 5,417,212 | A | 5/1995 | Szeles |
| 7,336,993 | B1 | 2/2008 | Szeles |
| 7,781,486 | B2 | 8/2010 | Szeles |
| 8,175,699 | B2 | 5/2012 | Szeles |
| 8,942,814 | B2 | 1/2015 | Szeles |
| 2004/0147995 | A1* | 7/2004 | Miazga ................ A61N 1/0551 607/142 |
| 2006/0206164 | A1* | 9/2006 | Gavronsky .......... A61H 39/002 607/46 |
| 2008/0039915 | A1* | 2/2008 | Van Den Biggelaar ................... A61N 1/0492 607/116 |
| 2010/0274327 | A1* | 10/2010 | Carroll ................ A61N 1/0456 607/72 |
| 2011/0257701 | A1* | 10/2011 | Strother ............... A61N 1/0456 607/46 |
| 2012/0022633 | A1 | 1/2012 | Olson et al. |
| 2014/0046423 | A1* | 2/2014 | Rajguru ............... A61N 1/0456 607/144 |

* cited by examiner

Primary Examiner — Ankit D Tejani
(74) Attorney, Agent, or Firm — Young Basile Hanlon & MacFarlane, P.C.

(57) ABSTRACT

A device for nerve stimulation therapy that includes at least one current generator, a housing having an outer surface and defining an interior cavity. The current generator includes a power supply and at least one current regulator, the and is configured to supply therapeutic current for a therapy interval. The device includes at least two leads electrically connected to the current generator and coupled to an associated electrode at least one electrode. The electrode has an insertion tip defined at the end of the electrode opposed to the lead such that the wherein the connection between the insertion tip and a central section of the electrode defines an angle that is not equal to 180 degrees.

15 Claims, 6 Drawing Sheets

ELECTROSTIMULATION DEVICE WITH PERCUTANEOUS LEADS

TECHNICAL FIELD

The present invention pertains to medical treatment therapies that utilize electrical stimulation of at least a portion of the nervous system of a patient for treating pain or other conditions. The present invention also pertains to devices for administering electrical stimulation to a patient having at least one penetrating electrode that is positioned in a semi-permanent manner relative to the body of the patient.

BACKGROUND

In recent years, therapies such as Percutaneous Electrical Nerve Stimulation (PENS) has been proposed and investigated for the management of acute and chronic pain syndromes, PENS is an analgesic therapy that combines advantages of both electro-acupuncture and TENS. PENS therapy utilizes acupuncture-like electrodes placed in the soft tissues to stimulate peripheral sensory nerves at the dermatomal level corresponding to a local pathology.

For many years, particular importance has been attached to stimulation of the vagus nerve. As the tenth cranial nerve, it is the main nerve of the parasympathetic system. It is also involved in the motor control of the larynx and pharynx and transmits taste sensations from the base of the tongue and sensations of touch from the pharynx, larynx and part of the external auditory canal (auricular branch).

Invasive stimulation of the vagus nerve in particular has in the meantime become an established therapeutic procedure in neurology for treatment of epilepsy: Prevention of intractable partial seizures has also been seen in certain instances due as a result of intermittent vagal stimulation in humans:

In the above, the patient's vagus nerve is exposed on the left region of the neck by neurosurgery and a current conductor is wound around it as an electrode. The device for generating current impulses is implanted under the skin in the left shoulder area. The vagus nerve stimulator can later be programmed from outside by means of an electromagnetic field. Electrical excitation of the vagus nerve causes a stimulation of the brain in various areas, as can be demonstrated by imaging methods.

Additional devices that have been employed in vagus nerve stimulation therapies include US Application No. 2012/022633 and U.S. Pat. No. 5,324,287 both to Szeles relate to devices that provide punctual stimulation of nerve endings located in the region of the ears, running to the brainstem nuclei. While such devices have been effective in treatment of certain medical conditions, usage is not without problems and drawbacks. The device disclosed in Szeles cannot be employed for extended periods. Additionally the device disclosed in Szeles lacks the flexibility to tailor treatment modalities to the specific needs and requirements of the patient and/or symptoms under treatment.

Thus it is desirable to provide a minimally invasive devise that can be robust and provide for enhanced performance over a variety of applications.

SUMMARY

A device for nerve stimulation therapy that includes at least one current generator contained in a housing that has an outer surface and defines an interior cavity. The current generator includes a power supply and at least one current regulator and is configured to supply therapeutic current for a therapy interval. The device also includes at least two leads electrically connected to the current generator that project from the housing to a location distal to the housing. The device also can includes at least one electrode member having a first end and an opposed second end that is operatively connectable with one of the leads. The electrode member has an insertion tip that is defined at the opposed second end of the body of the electrode. The insertion tip is contiguously connected to a central body section and defines an angular orientation between the central body section and the insertion tip. The electrode may also include a landing pad that is located at the first end of the electrode member. The landing pad is configured to be in electrical contact with the central body section of the electrode and projects outward therefrom.

DESCRIPTION OF THE DRAWING

In order to better understand the device as disclosed herein, reference is made to the following drawing figures which are to be considered illustrative of the device and methods as disclosed herein and are not to be construed as limitative and in which like reference numerals are employed to denote like elements throughout the several drawing views and in which.

DETAILED DESCRIPTION

A number of sites on the human body are characterized by nerve rich regions located in the skin or in the region immediately below the skin that have stimulus conduction connection with the central nervous system of an associated individual. One non-limiting example of such is the vagus nerve, CN X, which has a cutaneous representation in at the aural region. Other cutaneous nerve representations include but are not limited to the accessory nerve, CN XI which has cutaneous representation in the upper limb(s). Additionally, there are various cutaneous representations that have more localized impact.

It is contemplated that the device disclosed herein can be removably positioned on a suitable position on the body of a patient to achieve therapeutic stimulation of the related or associated nerve bundle. By way of non-limiting example, the device for nerve stimulation therapy as disclosed herein can be positioned proximate to the cutaneous presentation of the vagus nerve typically found at the auricle region of the outer ear.

Figure 1:
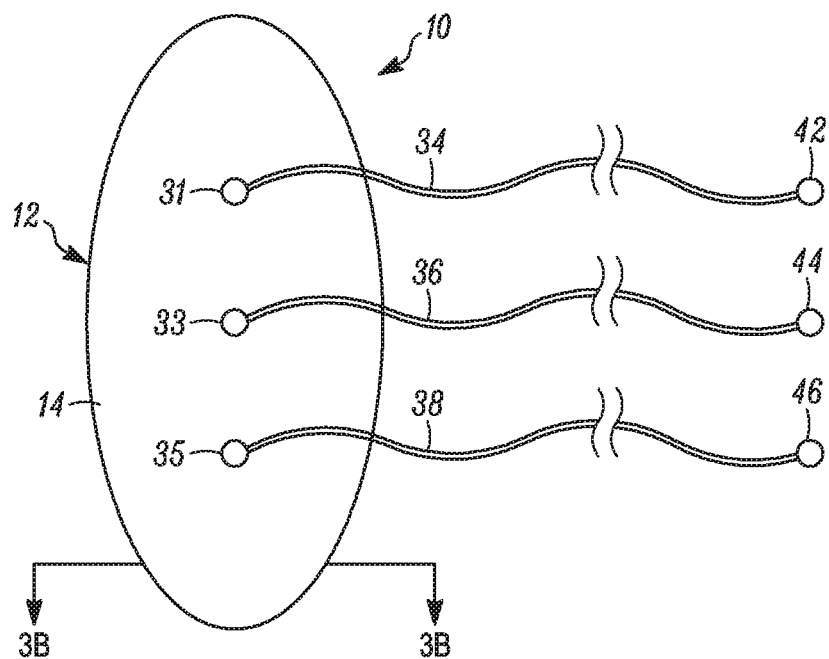
FIG. 1 is a schematic diagram of an embodiment of the device as disclosed herein.
Figure 2:
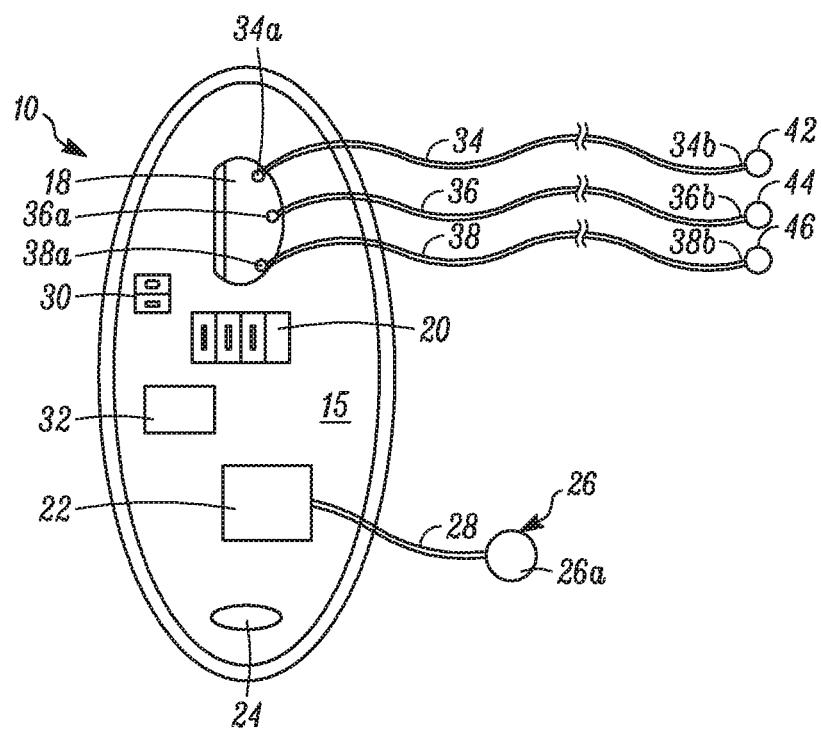
FIG. 2 is a schematic view of an embodiment of the housing of FIG. 1 with the upper portion of the housing removed.
Figure 8:
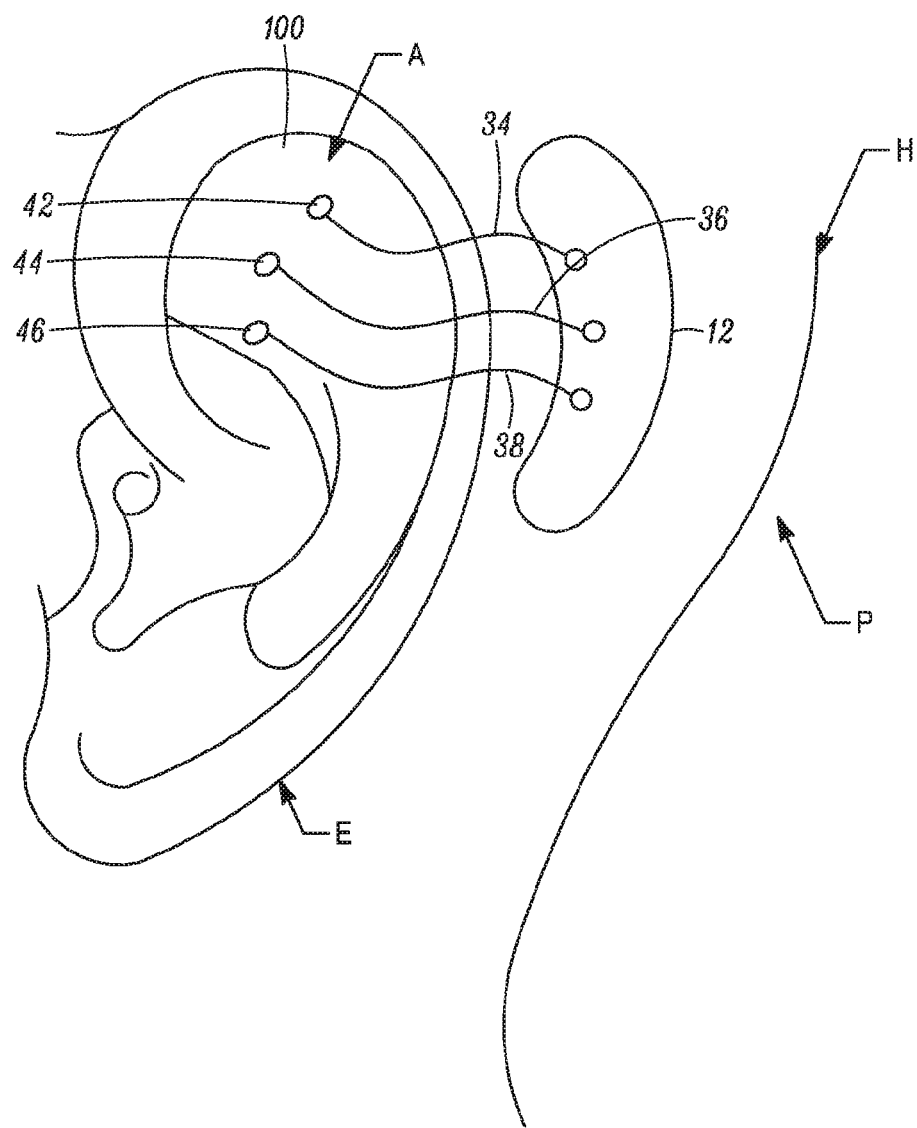
FIG. 8 is a plan view of an embodiment of the device as disclosed in position on an auricle of a patient.

The device 10 for nerve stimulation therapy can be configured in the manner depicted in FIGS. 1 and 2. The device 10 includes a housing 12 that has an outer surface cover 14 and a base 15 that function together to define an inner cavity 16. In the embodiment depicted the base 15 can have an ovoid elongate configuration as illustrated in FIGS. 1 and 2. In certain embodiments the housing 12 can have a crescent configuration. One such configuration is depicted in FIG. 8. In such configurations the such with a corresponding configuration in the associated outer surface cover 14. Outer surface cover 14 and the base 15 can have suitable mating geometries. It is contemplated that the housing 12 can have a configuration that is adapted to be removably attached to the skin region of the patient P generally proximate to the vagus nerve bundle region of interest. In the embodiment specifically discussed herein, the housing is configured to be removably attached to the skin of the patient P proximate to the outer ear of the patient.

In certain embodiments, the base 15 can have a generally planar central region 15a that is surrounded on its periphery by an upwardly extending ridge 15b that can be matingly connected to a corresponding region of the outer surface cover 14. In the embodiment depicted, the upwardly extending ridge 15b can be configured with a lip member 15c that is configured to receive a corresponding region configured on the outer surface cover 14.

Figure 4A:
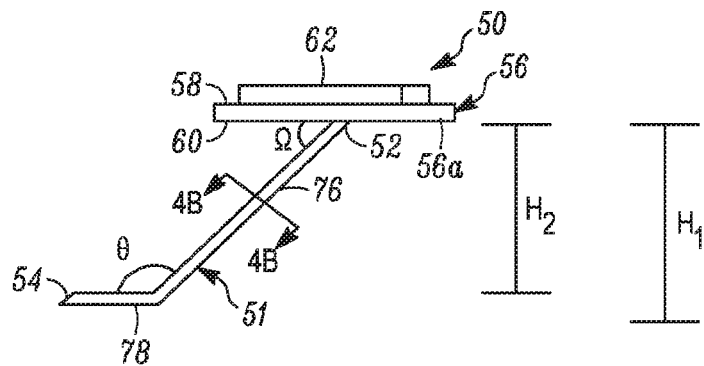
FIG. 4A is a side view of an embodiment of an electrode as disclosed herein.
Figure 4B:
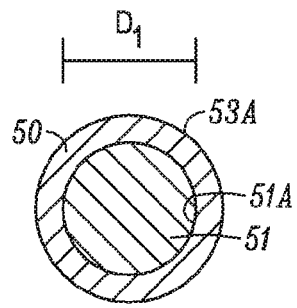
FIG. 4B is a cross section taken through the 4B-4B line of FIG. 4B.

The outer surface cover 14 can have a suitable configuration to mate with the base 15 and define the inner cavity 16 sufficient to receive and contain inner components that will be discussed in detail subsequently. The housing 12 has a wall member 14a. In the embodiment depicted in FIGS. 4A and 4B the wall member 14a is a continuous curve. It is also contemplated that other cross sectional configurations can be employed where desired or required. Non-limiting examples of such cross-sectional configurations include various rectilinear cross section as well as other complex configurations.

The wall member 14a can have a lip region 14b that extend around the peripheral edge 14b to define a shoulder 14c configured to contact the lip member 15c of the base 15. The base 15 and outer surface cover 14 can be joined in a manner that provided a generally permanent junction between the two elements such that the bond is generally resistant and/or impervious to the external environment. This can be accomplished by processes such as ultrasonic welding, adhesive bonding or the like.

While the housing 12 has been disclosed as a two-component member, it is also considered to be with in the purview of this disclosure that the outer surface cover 14 and base 15 can be configured as a single component member having a clamshell configuration connected by a living hinge or the like.

Where desired or required, the housing 12 can also include a suitable contact pad 17 affixed to the region of the housing that will contact the skin of the associated patient P. In the embodiment depicted in the drawing figures, the contact pad 17 is connected to at least a portion of an outwardly oriented face 15d defined on the base 15. The outwardly oriented face 15d is opposed to the inner cavity 16. The contact pad 17 can have a configuration that corresponds to the geometry of the base 15. In the embodiment depicted the contact pad 17 can include a housing contacting face 17a, a central body 17b that can be composed of a flexible foam material and a body contacting face 17c that is generally opposed to the housing contacting face 17a. The contact pad 17 is configured to provide suitable electrical and electronic grounding for the device 10 and may include a suitable adhesive material positioned on at least a portion of the body contacting face 17c to affix the device 10 in position on the skin of the patient P. Where the body contacting face 17c of the contact pad 17 is configured with an adhesive, the contacting face 17 can be overlain with a suitable removable release sheet 17d that is kept in place prior to device placement.

The device 10 is configured to deliver a suitable therapeutic current for a suitable interval or intervals when in place in the use position and activated. The device 10 can include at least one current generator 18 (see FIG. 2). In the embodiment depicted, the current generator 18 can be housed in the cavity 16 defined by the housing 12. The current generator 18 is configured to produce and supply therapeutic current for a desired therapeutic interval.

Figure 9:
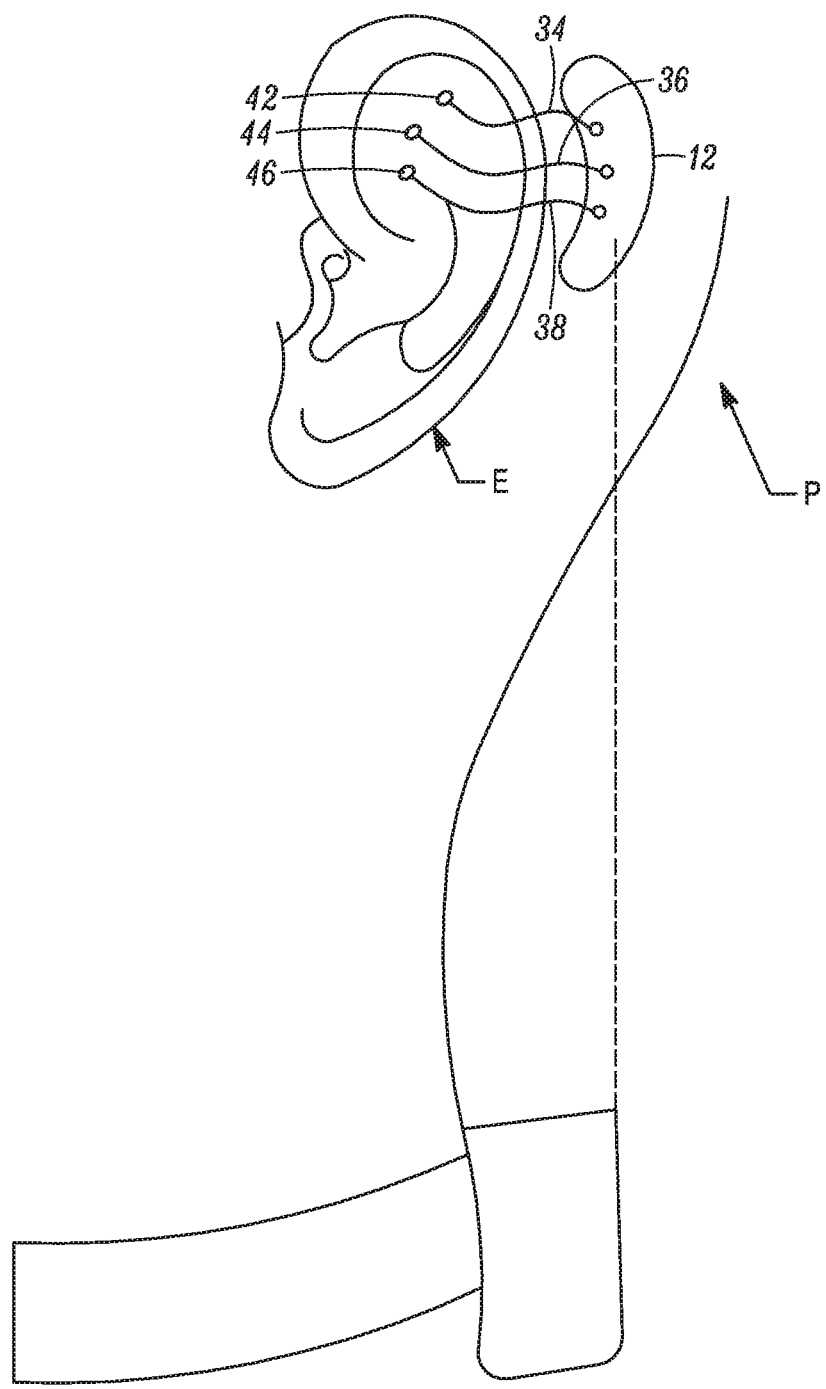
FIG. 9 is a schematic perspective view of an alternate embodiment of the device as disclosed herein.

As used herein, the term "therapeutic current" is taken to mean electric current that is delivered at a voltage suitable to stimulate the associated underlying nerve subsystem when the electric current is delivered to a suitable cutaneous representation of the underlying nerve or nerve system. With reference to FIGS. 8 and 9, the cutaneous representation can be located in the auricle region A of ear E is depicted as reference numeral 108. The amount of current that will be delivered is that sufficient to induce a responsive therapeutic effect on the targeted portion of the nervous system or affected tissue associated tissues, organs, organ systems or the like. It is contemplated that the current produced and delivered will be in an amount between about 0.25 millivolts and 5 millivolts, with therapeutic current delivered in a range between 0.5 and 4 millivolts in certain applications.

The device 10 can also include or be associated with a suitable energy storage source to provide power the current generator 18. This which can be one or more energy storage devices such as battery 20 which can be electrically coupled to current generator 18 in any suitable manner. It is contemplated that the battery 20 can be single use or rechargeable as desired or required. It is also contemplated that the battery 20 can be replaced in whole or in part with a suitable transceiver that is configured to receive and transmit wirelessly transmitted operating current during operation, recharge intervals or both.

The device 10 can also include a suitable onboard controller such as on board controller 22 that is operatively connected to the current generator 18 and other elements in the device 10 to regulate one of more of current strength, pulse duration, therapy interval and the like while the device 10 is in operation. The on board controller 22 can also be configured with suitable timers, chronometers, data storage modules and the like as desired or required.

Where desired or required, on board controller 22 can also regulate recharge processes where desired or required. The on board controller 22 may contain preprogrammed logic that operates the device 10. It is also contemplated that the on board controller 22 can be configured to receive and process inputted commands from one or more suitable externally positioned source(s) (not show). Where the on board controller 22 is configured to receive and process inputted commands from one or more suitably externally positioned source(s), it is contemplated that the device 10 can be configured with a suitable user interface such as receiver 24. Receiver 24 is operatively connected to the on board controller 22 and is configured to receive and process externally originated commands and instructions and to transmit externally oriented signals if desired or required.

The device 10 also can optionally include one or more sensors such as sensor 26. The sensor such as sensor 26 is one that is configured to monitor one or more relevant vital signs or other biological indicators of the associated patient P. Patient monitoring can proceed prior to during or after operation of the device 10. In the embodiment depicted, the sensor 26 is connected to the controller 22 via sensor lead 28. It is also considered to be within the purview of this disclosure that the sensor 26 can be configured so as to provide wireless feedback communication with the controller 22. Suitable logic can be resident in the on board controller 22 or other suitable processor to adapt or modify performance of the device 10 based on patent conditions as determined by sensor input as desired or required. The sensor 26 can have an housing 26a that has any configuration that will permit it to be removably and operatively affixed to the body of patient P to monitor and collect relevant data.

Figure 3A:
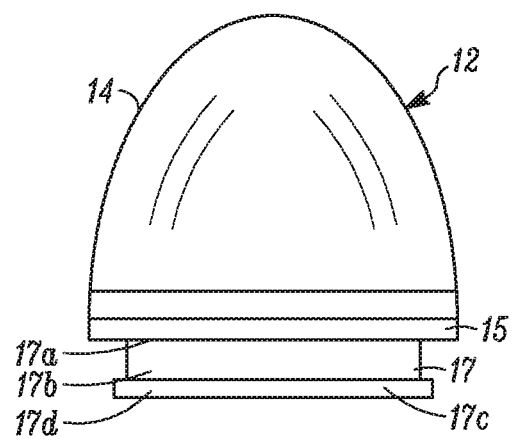
FIG. 3A is a side view of an embodiment of the housing of the device depicted in FIG. 1.
Figure 3B:
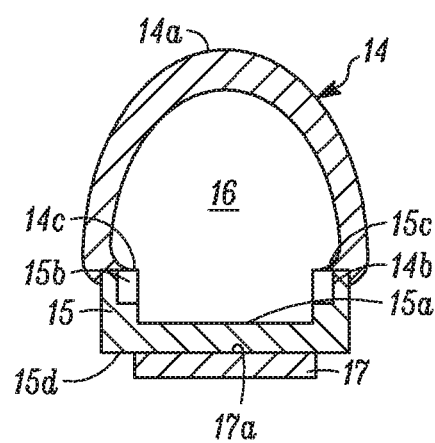
FIG. 3B is a cross sectional view of the housing taken though the 3A-3A line of FIG. 1

In the device 10 depicted in drawing FIG. 3, there is also an on-off switch 30. It is contemplated that the on-off switch 30 can be either manually operable, in which case the on-off switch 30 can have a suitable though housing fitting (not shown), or can be configured to respond to a command signal originating external to the device 10. The device 10 may also be configured with suitable data storage unit 32 to collect and maintain information regarding device performance, patient biofeedback and the like as desired or required. Such information can be compiled and outputted when required as by the patient's medical treatment personnel etc. It is also contemplated that the collected and stored feedback information can be utilized to modify and customize device 10 performance.

The device 10 also includes at least two current output leads. The number of current output leads and length of the given leads will be that appropriate for the specific nerve stimulation to be administered. In the embodiment depicted, the device 10 is configured with three current output leads 34, 36, 38, however it is within the purview of this invention to have more as desired or required.

In general, the current output leads 34, 36, 38 will be composed of thin flexible material capable of delivering the therapeutic current at the level desired or required. The leads 34, 36, 38 can each include a first end 34a, 36a, 38a that is operatively connected to the device 10 and an opposed terminal end 34b, 36b, 38b opposed to the respective first end. It is also contemplated that the one or more of the leads 34, 36, 38 can be configured to carry or transmit data and, as such can include one or more data leads to convey data to or from the respective second end 34a, 36a, 38a.

The current output leads 34, 36, 38 can be electrically coupled to the device 10 in any suitable manner. In the embodiment depicted in the various drawing figures, the respective first ends 34a, 36a, 38a of the current output leads 34, 36, 38 are permanently to the device 10 by soldering, mechanical connection or the like. However, it is considered within the purview of this disclosure that one or more of the leads 34, 36, 38 can be removably connected to the device 10 in any suitable manner. In the embodiment as illustrated in the drawing figures, the first end 34a, 36a, 38a of respective lead 34, 36, 38 will be connected to current generator 18. The leads 34, 36, 38 can extend through the one or more suitable one or more through bores defined in housing 12. In the embodiment depicted, the leads 34, 36, 38 extend through though bores 31, 33, 35 defined in the outer surface cover 14.

The leads 34, 36, 38 will each have a suitable length to permit location of the housing 12 and its associated internal devices controls and circuitry at a suitable position relative to the patient P undergoing treatment. In many applications, it is contemplated that the housing 12 will be removably affixed to the patient by suitable removable or temporary adhesive. The housing 12 can be affixed at any suitable location that is generally proximate to the cutaneous access location selected to the target subsection of the nervous system for the treatment process desired. In instances where the vagus nerve is the portion of the nervous system to be accessed, it is contemplated that the housing 10 can be located proximate to that access location. For example, the housing 12 can be located on the head region behind the associated ear E of the patient P who is to be treated. It is considered to be within the purview of this disclosure that the other access locations can be employed and that the housing 12 will be located accordingly.

The terminal end 34b, 36b, 38b of one or more of leads 34, 36, 38 will be in electrical contact with an associated electrode such as electrode 50. It is contemplated that the lead 34, 36 or 38 can be directly connected to the associated electrode 50 if desired or required. It is also within the purview of this disclosure that the respective terminal ends 34b, 36b, 38b of one or more electrodes 34, 36, 38 be configured with a respective suitable coupler 40, 42, 44. Couplers 40, 42, 44 are configured to engagingly contact an associated electrode such as electrode 50 in any suitable manner to establish electrical contact with the electrode 50. "Engaging contact" as that term is used herein can include permanent connection, detachable contact etc. between the associated electrode 50 and the respective coupler 40, 42, 44 and associated lead 34, 36, 38. In certain applications, at least one of the couplers 40, 42, 44 is configured with a surface or element that can matingly engage the associated electrode 50 in an electrically conductive manner. Non-limiting examples of such engagement will be discussed subsequently.

The electrode 50 employed will be one that can be positioned on the patient P in a removable subcutaneous manner. As used herein, the term "subcutaneous manner" is defined to include, but not be limited to, locations that as extend into the region of the skin of the patient P which is generally defined as the subcutaneous region. Also included in this definition are adjacent regions such as the dermal region.

Figure 5:
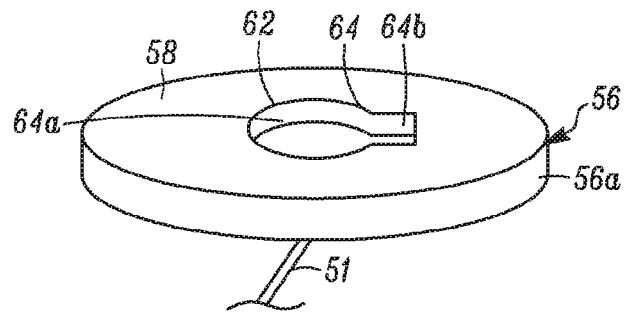
FIG. 5 is a top view of the electrode of FIG. 4.

An embodiment of one suitable electrode configuration is depicted in FIGS. 4 and 5. The electrode 50 has projection member 51 that has a first end 52 configured to be capable of electrical connection to an associated lead 34, 36, 38. It is within the purview of this disclosure to that the electrical connection can be removable or permanent as desired or required. The projection member 51 also has a second end 54 that is distal to first end 52. The projection member 51 can be composed of any suitable electrically conductive material that is suitable for sort term contact in the subcutaneous and or dermal region of the patient. Where desired or required, the projection member 51 can also include a suitable nonconductive material 53 or sheath that extends over a portion of the outer surface 51a of the projection member to isolate a portion of the projection member 51 from the tissue proximate to the outer surface 53a of the outer sheath 53. It is contemplated that where projection member 51 is configured with a sheath 53, the region proximate to the second end 54 will be unsheathed such that the outer surface 51a of projection member 51 will be in contact with the surrounding tissue of the patient P when the electrode is in the use position.

The electrode 50 will include at least one region configured to be in electrical contact with an associated lead 34, 36, 38. It is contemplated that the associated lead 34, 36, 38 can be directly connected to the desired electrode 50 in any suitable manner as desired or required. It is also within the purview of this disclosure that the associated lead 34, 36, 38 and electrode 50 may be configured to be in removable contact with one another. Such removable contact may facilitate the placement of the electrode 50 in position on the body of a patent prior to connection with the lead 34, 36, 38 and the associated device 10.

Where desired or required, the first end 52 of projection member 51 of electrode 50 can be connected to a suitable landing pad 56 that can facilitate connection, either removable or permanent, with the associated lead 34, 36, 38. In the embodiment depicted in FIGS. 4 and 5, the landing pad 56 is contiguously connected to the first end 52 of projection member 51. The landing pad 56 can have any configuration suitable to seat and connect the associated leads 34, 36 or 38 relative to the associated electrode 50. The configuration of the landing pad 56 can also facilitate positioning of the associated electrode 50 in the dermal region of the patient P at suitable depth and location. In the embodiment depicted, the landing pad 56 is configured as planar member having a central body 56a an outwardly oriented face 58 and an opposed, inwardly oriented face 60 that that is generally contiguous with the first end 52 of the projection member 51 when the electrode 50 is in the use position. The landing pad 56 can have any suitable planar configuration and can be circular, rectangular, etc.

Where desired the outwardly oriented face 58 of landing pad 56 can be configured to directly engage the associated lead 34, 36, 38 or coupler 42, 44, 46. Alternately, the landing pad 56 can also include a mating member 62 that is configured to contact and matingly engage either the associated lead 34, 36, 38 or the coupler 42, 44, or 46 as desired or required. The mating member 62 can be contiguously formed with the landing pad 56 and project outwardly from the upwardly oriented face 58. It is also contemplated that the mating member 62 can be configured as a distinct element that is connected to the landing pad 56 in an electronically conductive manner.

In the embodiment depicted in FIGS. 4 and 5, the mating member 62 is configured as an outwardly oriented projection 64 that extends outward from the outwardly oriented face 58 of the landing pad 56. The projecting member 64 has a suitable mating configuration. In the embodiment as depicted in the drawing figures, the projecting member 64 has a generally oval or circular projection region 64a that is configured with a suitable locking member such as a key slot region 64b.

Figure 6:
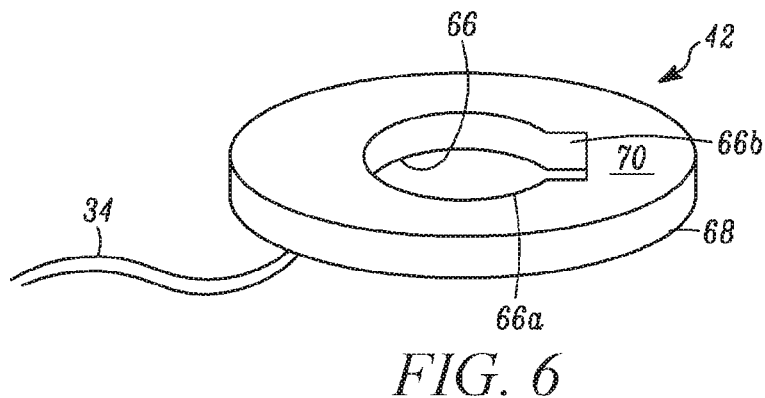
FIG. 6 is a detail view of an embodiment of a connector member of a lead as depicted herein.
Figure 7:
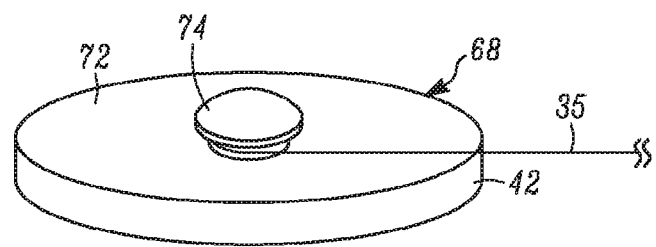
FIG. 7 reverse view of the connector of FIG. 6 viewed from the bottom.

The projecting member 64 is configured to be matingly received in a corresponding orifice 66 defined in the first face 70 of the planar body 68 of a suitable coupler 42, 44, or 46. In the embodiment as depicted in FIGS. 6 and 7 the corresponding orifice 66 can be configured with an oval or circular region 66a and a contiguous key slot 66b. It is contemplated that the first face 70 of the planar body 68 is configured to be oriented in facing relation to the outwardly oriented face 58 of the landing pad 56 of electrode 50 when in the engaged or use position.

It is also contemplated that one or more of the couplers 42, 44, 46 can have suitable lead-engaging region. The coupler 42, 44, or 46 can be integrally connected to the respective lead 34, 36, 38 in any suitable manner. In the embodiment depicted, the respective terminal end 34b, 36b, 38b of the associated lead 34, 36, 38 can be wound around head 74 projecting outward from opposed face 72 of the planar body 68 the landing pad and affixed thereto. The head 74 projecting from the planar body 68 of the landing pad 56 can have any suitable configuration. In the embodiment depicted, the head 74 has a cylindrical configuration.

It is also within the purview of this disclosure to configure the two respective engaging members in a snap fit configuration or employ other engagement devices as desired or required. In certain applications, it is contemplated that the engagement mechanism will be configured to permit or facilitate a break-away connection in the event that the lead 34, 36, 38 is snagged of otherwise compromised.

The elongated body 51 of electrode 50 includes an insertion tip section 78 located distal to the landing pad 56. In the embodiment depicted in FIGS. 4A and 10, the elongated body 51 includes a first central body section 76 that is located proximate to the first end 52 with the insertion tip section 78 that located distal to that first central body section 76. The first and second sections 76, 78 are connected to one another such that the ultimate junction between the first and second sections 76, 78 forms an angle Θ that is less than 180°. In various embodiments, the angle can be less than 160°, with angles between 95° and 130° being employed in certain embodiments. The orientation at the junction between the first and second sections 76, 78 can be angular or arcuate as desired or required.

In configurations where the elongated body 51 is connected to a landing pad 56, it is contemplated that an angle Ω is formed between the inwardly oriented face 60 of the landing pad 56 and the central body portion 76 of the elongated body 51. In the embodiment depicted in FIG. 4, the angle Ω will have a value between 30° and 90°; with angles between 30° and 75° being present in certain specific embodiments.

The second or distal end 54 of the elongated member 51 can be configured to pierce the skin of the patient to which the device is to be affixed and employed. The distal end 54 can be pointed or can have any suitable geometry to accomplish this end. The electrode 50 can have a height $H_1$ measured from first end 52 to second end 54 sufficient to place the at least a portion of the tip 54 and, if possible, a portion of the tip section 78 into electrical contact with the nerve ending cluster of choice. In certain embodiments, the height $H_1$ can be between 0.5 mm and 5 mm. In certain applications, it is contemplated that the height $H_1$ will be between 1.0 mm and 4 mm, while in other applications it is contemplated that the height $H_1$ can be between 1.0 and 3 mm. The height $H_2$ of the central body portion 76 will be less than the total height $H_1$. In certain embodiments, $H_2$ will have a value that is between 60% and 95% of the value of $H_1$.

The diameter $D_1$ of the elongated body 51 of the electrode will be in a range sufficient to permit insertion into the dermal (and possibly outermost portions of the hypodermis) and placement relative thereto and to deliver the therapeutic electrical current to the identified nerve regions. In certain embodiments, it is contemplated that the diameter $D_1$ of the elongated member 51 can be between about 0.18 mm and about 1.5 mm in certain applications exclusive of the tip region 54 diameter. The elongated member 51 can have a constant diameter or can decrease along the length of the elongated member 51.

In certain embodiments of the electrode 50, it is contemplated that the first central body section 76 has a length between 0.5 and 4 mm and that the second insertion tip section 78 can have a length that is between 10 and 40% of the first central body section length. In certain applications, it is contemplated that the insertion tip section 78 will have a length between 0.25 and 1 mm.

Figure 10:
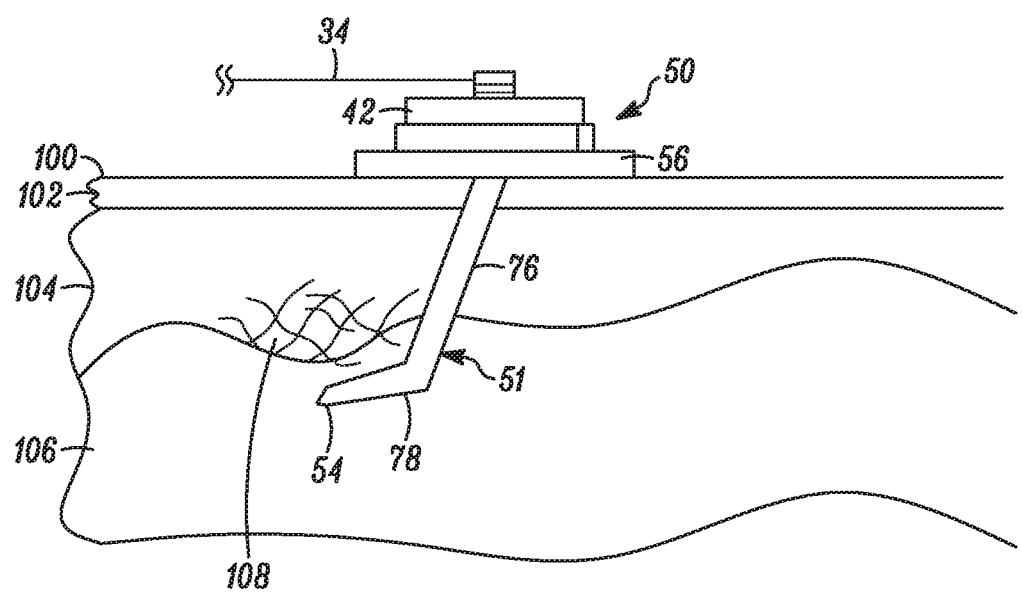
FIG. 10 is a side view of FIG. 4 as inserted and in position on a patient.

When the electrode 50 is in the use position and the device 10 is employed for therapeutic purposes, the electrode 50 and associated lead 34, 36, or 38 and contacts 42, 44, 46 can be removably inserted into the skin region of the patient in the region of the nerve to be accessed. One non-limiting example of an insertion strategy is as follows. When in place, the elongated body region 51 projects into the skin region 100 of the patient P through the epidermis 102 and into the dermis 104. As illustrated in the embodiment depicted in FIG. 10, is contemplated that the elongated body region 51 can be configured to terminate in the dermis or upper regions of the hypodermis depending on the general location of nerves to be accessed. In the embodiment illustrated in FIG. 10, when the electrode 50 is in place, it projects into the skin region 100 of the patient such that the elongated body can be configured to dermis 104 or the upper regions of the hypodermis 106 depending on the general location of the nerves to be accessed. In this scenario, the nerve region 108 is located at the junction between dermis 104 and hypodermis 106.

The inwardly facing surface 60 of landing pad 56 can be in overlying or overlying contacting orientation with the outer surface of epidermis with the associated contact 42, 44, or 46 being in stacked overlying relation to the landing pad 56.

One non-limiting example of a therapeutic application location is illustrated in FIG. 8 in which the vagus nerve is accessed for nerve stimulation therapy via the auricle region A located in the ear E of patient P. Electrode(s) 50 are positioned in appropriate regions of the auricle A by insertion into the skin region 102. Once in position, the electrode(s) can be connected to the associated lead(s) 34, 36, 38 by engagement to coupler(s) 42, 44, 46. The housing 12 of device 10 can be positioned at a suitable location as on the lower scalp or head region H of the patient P proximate and behind the auricle region A of the associated ear E by suitable means such as a removable adhesive.

Either during the positioning of the device 10 or once the device 10 is in position, the current generator 18 can be activated by suitable means such as the on-off switch 30 and electrical stimulation can proceed according to the parameters programmed into the device 10 either at the factory or provided via the user interface 24.

In an alternate power embodiment, power source and receiver/battery will use wireless power transfer (WPT) via resonant inductive coupling to send and receive power signals. Resonant inductive coupling, or electrodynamic induction, is the near field wireless transmission of electrical energy between two magnetically coupled coils that are part of resonant circuits tuned to resonate at the same frequency. Resonant transfer functions by utilizing a coil ring with an oscillating current. This generates an oscillating magnetic field. Because the coil is highly resonant, any energy placed in the coil dies away relatively slowly over very many cycles; but if a second coil is brought near it, the coil can pick up most of the energy before it is lost, even if it is some distance away.

This technology is developed for powering and charging portable devices such as cell phones and tablet computers at a distance, without being tethered to an outlet. Resonant energy transfer is the operating principle behind proposed short range (up to 2 meters) wireless electricity systems such as WiTricity or Rezence and systems that have already been deployed, such as Qi power transfer, passive RFID tags and contactless smart cards. In the early 1960s resonant inductive wireless energy transfer was used successfully in implantable medical devices including such devices as pacemakers and artificial hearts. Today resonant inductive energy transfer is regularly used for providing electric power in many commercially available medical implantable devices.

The power source will transmit energy via an electromagnetic field to a receiver which can store energy in a battery, and in turn, send electrical impulses to the percutaneous Leads which are connected to subject at medically indicated sites. The power source and Receiver may each have features which enable modulated power distribution. When employed, the power source can transmit energy via an electromagnetic field to a receiver which can store energy in a battery, and in turn, send electrical impulses to the percutaneous leads which are connected to subject at medically indicated sites. The power source and receiver may each have features which enable modulated power distribution While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A device for providing nerve stimulation therapy to a patient, the device comprising:
    at least one current generator contained in a housing having an outer surface and defining an interior cavity, the current generator including a power supply and at least one current regulator, the current generator configured to supply therapeutic current for a therapy interval;
    at least two leads electrically connected to the current generator, the leads projecting from the housing to a location distal to the housing;
    at least one nerve stimulation electrode having a landing pad, and a projection member in electrical connection with the landing pad, the projection member having a central body section having a first end connected to the landing pad at an angle that is not equal to 900 and an opposed second end, the projection member having an insertion tip section contiguously connected to the central body section, the insertion tip section having an insertion tip defined at the opposed second end of the electrode, the first end of the electrode operatively connectable with one of the at least two leads at the location distal to the housing, wherein the connection between the insertion tip section and the central body section defines an angle that is not equal to 180 degrees.

2. The nerve stimulation therapy device of claim 1 wherein the landing pad has a thickness T and a width W and a first inwardly oriented face and a second outwardly oriented face opposed to the first inwardly oriented face, the first inwardly oriented face and the second outwardly oriented face separated by the thickness T, wherein the central body section of the at least one electrode projects from the first inwardly oriented face and wherein the width W is greater than the thickness T.

3. The nerve stimulation therapy device of claim 1 wherein the central body section of the electrode is an elongated body having a central body section length; wherein the
insertion tip section has a tip section length such that the tip section length is less than the elongated body length, and the tip section is configured to removably pierce an epidermal layer of skin.

4. The nerve stimulation therapy device of claim 3 wherein the tip section length is less than 30% of the central body section length.

5. The nerve stimulation therapy device of claim 1 wherein the electrode has a height from first end to opposed second end that is between 1 mm and 3 mm.

6. The nerve stimulation therapy device of claim 1 wherein the landing pad is an elongate planar element contiguously connected to the central body section of the electrode such that the central body section projects laterally outward therefrom.

7. The nerve stimulation therapy device of claim 6 wherein the landing pad has at least one region configured to matingly contact the distal region of one of the at least two leads, the at least one region including an electrical contact projection contagiously joined to the second outwardly oriented face of the landing pad and projecting outward therefrom;
wherein at least one of the leads includes a coupler, the coupler in electronic contact with the lead and positioned at a location distal to the housing, the coupler having a planar body and at least one orifice defined therein, the orifice configured to receive the electrical contact projection telescopically therein.

8. The nerve stimulation therapy device of claim 1 further comprising a non-conductive coating overlying at least a portion of the central body section of the electrode.

9. The nerve stimulation therapy device of claim 1 further comprising a grounding pad connected to at least a portion of the outer surface of the housing.

10. The nerve stimulation therapy device of claim 9 wherein the current generator is configured to deliver electric current in an amount between 1 and 4 millivolts to the at least two leads.

11. The nerve stimulation therapy device of claim 10 further comprising at least one on-board control device and at least one user interface configured to receive at least one command originating remote to the housing.

12. The nerve stimulation therapy device of claim 9 wherein the housing is configured to be removably attached to a skin region of the patient, the housing comprising:
a base, the base having a planar region and an outer periphery and an upwardly extending ridge located proximate to at least a portion of the outer periphery; and
a cover, the cover having a region configured to contact the upwardly extending ridge defined on the base, wherein the base and the cover define an inner cavity.

13. The nerve stimulation therapy device of claim 12 wherein the housing further comprises a contact pad, the contact pad affixed to at least a portion of an outwardly oriented face of the base, the contact pad configured to removably contact skin of the patient.

14. A device for providing nerve stimulation therapy to a patient, the device comprising:
at least one current generator contained in a housing having an outer surface and defining an interior cavity, the current generator including a power supply and at least one current regulator, the current generator configured to supply therapeutic current for a therapy interval;
at least two leads electrically connected to the current generator, the leads projecting from the housing to a location distal to the housing;
at least one electrode having a landing pad, and a projection member in electrical connection with the landing pad, the projection member having a central body section having a first end connected to the landing pad at an angle that is not equal to 90° and an opposed second end, the projection member having an insertion tip section contiguously connected to the central body section, the insertion tip section having an insertion tip defined at the opposed second end of the electrode, the first end of the electrode operatively connectable with one of the at least two leads at the location distal to the housing, wherein the connection between the insertion tip section and the central body section defines an angle that is not equal to 180 degrees;
wherein the housing is configured to be removably attached to a skin region of the patient, the housing comprising:
a base, the base having a planar region and an outer periphery and a upwardly extending ridge located proximate to at least a portion of the outer periphery; and
a cover, the cover having a region configured to contact the upwardly extending ridge defined on the base, wherein the base and the cover define an inner cavity; and
a contact pad, the contact pad affixed to at least a portion of an outwardly oriented face of the base, the contact pad configured to removably contact the skin of the patient.

15. The nerve stimulation therapy device of claim 14:
wherein the landing pad has at least one region configured to matingly contact the distal region of one of the at least two leads, the at least one region including an electrical contact projection contagiously joined to the outwardly oriented face of the landing pad and projecting outward therefrom:
wherein at least one of the leads includes a coupler, the coupler in electronic contact with the lead and positioned at a location distal to the housing, the coupler having a planar body and at least one orifice defined therein, the orifice configured to receive the electrical contact projection telescopically therein.

* * * * *